United States Patent
Singleton et al.

(10) Patent No.: US 6,271,432 B2
(45) Date of Patent: Aug. 7, 2001

(54) FISCHER-TROPSCH ACTIVITY FOR NON-PROMOTED COBALT-ON-ALUMINA CATALYSTS

(75) Inventors: Alan H. Singleton, Baden; Rachid Oukaci, Gibsonia; James G. Goodwin, Cranberry Township, all of PA (US)

(73) Assignee: Energy International, Pittsburgh, PA (US)

( * ) Notice: Subject to any disclaimer, the term of this patent is extended or adjusted under 35 U.S.C. 154(b) by 0 days.

(21) Appl. No.: 09/742,873

(22) Filed: Dec. 20, 2000

Related U.S. Application Data

(62) Division of application No. 09/320,327, filed on May 26, 1999, now Pat. No. 6,191,066.
(60) Provisional application No. 60/086,846, filed on May 27, 1998.
(51) Int. Cl.[7] ............... C07C 2/00; C07C 1/00; C07C 4/00; C07C 27/06; C07C 27/00
(52) U.S. Cl. .......... 585/700; 585/733; 518/700; 518/715
(58) Field of Search .................... 585/700, 733; 518/700, 715

(56) References Cited

U.S. PATENT DOCUMENTS

| | | | | |
|---|---|---|---|---|
| 2,393,909 | * | 1/1946 | Johnson | 260/449.6 |
| 2,515,245 | * | 7/1950 | Mattox | 252/417 |

* cited by examiner

*Primary Examiner*—Mark L. Bell
*Assistant Examiner*—Patricia L. Hailey
(74) *Attorney, Agent, or Firm*—Fellers, Snider, Blankenship, Bailey & Tippens

(57) ABSTRACT

Cobalt catalysts, and processes employing these inventive catalysts, for hydrocarbon synthesis. The inventive catalyst comprises cobalt on an alumina support and is not promoted with any noble or near noble metals. In one aspect of the invention, the alumina support preferably includes a dopant in an amount effective for increasing the activity of the inventive catalyst. The dopant is preferably a titanium dopant. In another aspect of the invention, the cobalt catalyst is preferably reduced in the presence of hydrogen at a water vapor partial pressure effective to increase the activity of the cobalt catalyst for hydrocarbon synthesis. The water vapor partial pressure is preferably in the range of from 0 to about 0.1 atmospheres.

13 Claims, 2 Drawing Sheets

FISCHER-TROPSCH ACTIVITY FOR NON-PROMOTED COBALT-ON-ALUMINA CATALYSTS

This application is a divisional of application Ser. No. 09/320,327 filed May 26, 1999, now U.S. Pat. No. 6,191,066, which claims the benefit of U.S. Provisional Application Ser. No. 60/086,846, filed May 27, 1998.

BACKGROUND OF THE INVENTION

1. Technical Field

The present invention relates to systems and processes for conducting hydrocarbon synthesis and to cobalt-on-alumina catalysts employed in such processes.

2. Background

In Fischer-Tropsch processes, a synthesis gas ("syngas") comprising carbon oxide(s) and hydrogen is reacted in the presence of a Fischer-Tropsch catalyst to produce liquid hydrocarbons. Certain advanced cobalt catalysts have proven to be very effective for Fischer-Tropsch synthesis. However, for these catalysts, extensive promotion with noble and/or near noble metals has been required in order to enhance the reducibility of the cobalt to an extent sufficient to achieve acceptable Fischer-Tropsch conversion activities. Due in significant part to the cost of obtaining and adding such promoters, these cobalt catalysts have typically been quite expensive. Thus, a need presently exists for a means of significantly reducing the cost of cobalt catalysts useful for Fischer-Tropsch synthesis while maintaining activity levels which are at least comparable to those heretofore obtained by promoting such catalysts with noble metals.

The "syngas" employed in Fischer-Tropsch processes can be produced, for example, during coal gasification. Processes are also well known for obtaining syngas from other hydrocarbons, including natural gas. U.S. Pat. No. 4,423,265 to Chu et al. notes that the major processes for producing syngas depend either upon (a) the partial combustion of the hydrocarbon fuel with an oxygen-containing gas, (b) the reaction of a hydrocarbon fuel with steam, or (c) a combination of these two reactions. U.S. Pat. No. 5,324,335 to Benham et al. explains the two primary methods (i.e., steam reforming and partial oxidation) for producing syngas from methane. The Encyclopedia of Chemical Technology, Second Edition, Volume 10, pages 3553–433 (1966), Interscience Publishers, New York, N.Y. and Third Edition, Volume 11, pages 410–446 (1980), John Wiley and Sons, New York, N.Y. is said by Chu et al. to contain an excellent summary of gas manufacture, including the manufacture of synthesis gas.

It has long been recognized that syngas can be converted to liquid hydrocarbons by the catalytic hydrogenation of carbon monoxide. The general chemistry of the Fischer-Tropsch synthesis process is as follows:

$$CO + 2H_2 \rightarrow (-CH_2-) + H_2O \quad (1)$$

$$2CO + H_2 \rightarrow (-CH_2-) + CO_2 \quad (2)$$

The types and amounts of reaction products, i.e., the lengths of carbon chains, obtained via Fischer-Tropsch synthesis can vary depending upon process kinetics and choice of catalyst.

Many attempts at providing effective catalysts for selectively converting syngas to liquid hydrocarbons have been disclosed. U.S. Pat. No. 5,248,701 to Soled et al., presents an over-view of relevant prior art. The two most popular types of catalysts heretofore used in Fischer-Tropsch synthesis have been iron-based catalysts and cobalt-based catalysts. U.S. Pat. No. 5,324,335 to Benham et al. discusses the fact that iron-based catalysts, due to their high water gas shift activity, favor the overall reaction shown in (2) above, while cobalt-based catalysts tend to favor reaction scheme (1).

The current practice is to support the catalytic components on porous, inorganic refractory oxides. Particularly preferred supports have included silica, alumina, silica-alumina, and titania. In addition, other refractory oxides from Groups III, IV, V, VI and VIII have been used as catalyst supports.

As mentioned above, the prevailing practice has been to also add promoters to the supported catalysts. Promoters have typically included noble metals, such as ruthenium, and near noble metals. Promoters are known to increase the activity of the catalyst, sometimes rendering the catalyst three to four times as active as its unpromoted counterpart. Unfortunately, effective promoter materials are typically quite costly both to obtain and to add to the catalyst.

Contemporary cobalt catalysts are typically prepared by impregnating the support with the catalytic material. As described in U.S. Pat. No. 5,252,613 to Chang et al., a typical catalyst preparation may involve impregnation, by incipient wetness or other known techniques, of, for example, a cobalt nitrate salt onto a titania, silica or alumina support, optionally followed or preceded by impregnation with a promoter material. Excess liquid is then removed and the catalyst precursor is dried. Following drying, or as a continuation thereof, the catalyst is calcined to convert the salt or compound to its corresponding oxide(s). The oxide is then reduced by treatment with hydrogen, or a hydrogen-containing gas, for a period of time sufficient to substantially reduce the oxide to the elemental or catalytic form of the metal. U.S. Pat. No. 5,498,638 to Long points to U.S. Pat. Nos. 4,673,993, 4,717,702, 4,477,595, 4,663,305, 4,822,824, 5,036,032, 5,140,050, and 5,292,705 as disclosing well known catalyst preparation techniques.

Fischer-Tropsch synthesis has heretofore been primarily conducted in fixed bed reactors, gas-solid reactors, and gas-entrained fluidized bed reactors, fixed bed reactors being the most utilized. U.S. Pat. No. 4,670,472 to Dyer et al. provides a bibliography of several references describing these systems.

Recently, however, considerable efforts have been directed toward conducting Fischer-Tropsch synthesis in three-phase (i.e., solid, liquid, and gas/vapor) reactors. One such system is the slurry bubble column reactor (SBCR). In a SBCR, catalyst particles are slurried in liquid hydrocarbons within a reactor chamber, typically a tall column. Syngas is then introduced at the bottom of the column through a distributor plate, which produces small gas bubbles. The gas bubbles migrate up and through the column, causing a beneficial turbulence, while reacting in the presence of the catalyst to produce liquid and gaseous hydrocarbon products. Gaseous products are captured at the top of the SBCR, while liquid products are recovered through a filter which separates the liquid hydrocarbons from the catalyst fines. U.S. Pat. Nos. 4,684,756, 4,788,222, 5,157,054, 5,348,982, and 5,527,473 reference this type of system and provide citations to pertinent patent and literature art.

It is recognized that conducting Fischer-Tropsch synthesis using a SBCR system could provide significant advantages over the reaction systems commonly employed heretofore. As noted by Rice et al. in U.S. Pat. No. 4,788,222, the potential benefits of a slurry process over a fixed bed process include better control of the exothermic heat produced by the Fischer-Tropsch reactions as well as better maintenance of catalyst activity by allowing continuous recycling, recovery and rejuvenation procedures to be implemented. U.S. Pat. Nos. 5,157,054, 5,348,982, and 5,527,473 also discuss advantages of the SBCR process. However, the slurry bubble column process has been expensive to operate, owing in part to the significant catalyst costs required.

SUMMARY OF THE INVENTION

The present invention provides "nonpromoted" cobalt-on-alumina catalysts unexpectedly and surprisingly having conversion activities at least comparable to those of the best promoted formulations. The inventive catalysts also exhibit superior product selectivity characteristics and are particularly effective for use in SBCR processes and other three-phase reaction systems. This remarkable discovery significantly decreases the cost of the Fischer-Tropsch conversion process, as the more expensive promoters need not be utilized to achieve acceptable results.

In one aspect, the present invention provides a cobalt catalyst for hydrocarbon synthesis. The cobalt catalyst comprises cobalt supported on a γ-alumina support. The catalyst is not promoted with any noble metals and is not promoted with any near noble metals. However, the γ-alumina support includes a dopant in an amount effective for increasing the activity of the catalyst for hydrocarbon synthesis. The dopant is preferably a titanium dopant.

In another aspect, the present invention provides a process for hydrocarbon synthesis comprising the step of reacting a synthesis gas in the presence of a cobalt catalyst. The cobalt catalyst comprises cobalt supported on a γ-alumina support. The cobalt catalyst is not promoted with any noble metals and is not promoted with any near noble metals. However, the γ-alumina support includes a dopant in an amount effective for increasing the activity of the cobalt catalyst for hydrocarbon synthesis. The dopant is preferably a titanium dopant.

In yet another aspect, the present invention provides a cobalt catalyst for hydrocarbon synthesis, wherein the cobalt catalyst comprises cobalt supported on a γ-alumina support. The cobalt catalyst is not promoted with any noble metals and is not promoted with any near noble metals. However, the cobalt catalyst has been reduced in the presence of hydrogen at a water vapor partial pressure effective to increase the activity of the cobalt catalyst for hydrocarbon synthesis. The water vapor partial pressure is preferably in the range of from 0 to about 0.1 atmospheres.

In yet another aspect, the present invention provides a process for hydrocarbon synthesis comprising the steps of: (a) reducing a cobalt catalyst in the presence of hydrogen and at a water vapor partial pressure effective to increase the activity of the cobalt catalyst for hydrocarbon synthesis and (b) reacting a synthesis gas in the presence of the cobalt catalyst. The cobalt catalyst is not promoted with any noble metals and is not promoted with any near noble metals.

In yet another aspect, the present invention provides a method of improving the activity of a cobalt catalyst for hydrocarbon synthesis, wherein the cobalt catalyst has an alumina support. The cobalt catalyst is not promoted with any noble metals and is not promoted with any near noble metals. However, the alumina support includes a titanium dopant in an amount, expressed as elemental titanium, of at least 500 ppm by weight of the total weight of the alumina support.

Further objects, features and advantages of the present invention will be apparent upon examining the accompanying drawings and upon reading the following description of the preferred embodiments.

DETAILED DESCRIPTION OF THE PREFERRED EMBODIMENTS

Catalyst Compositions

Figure 1:
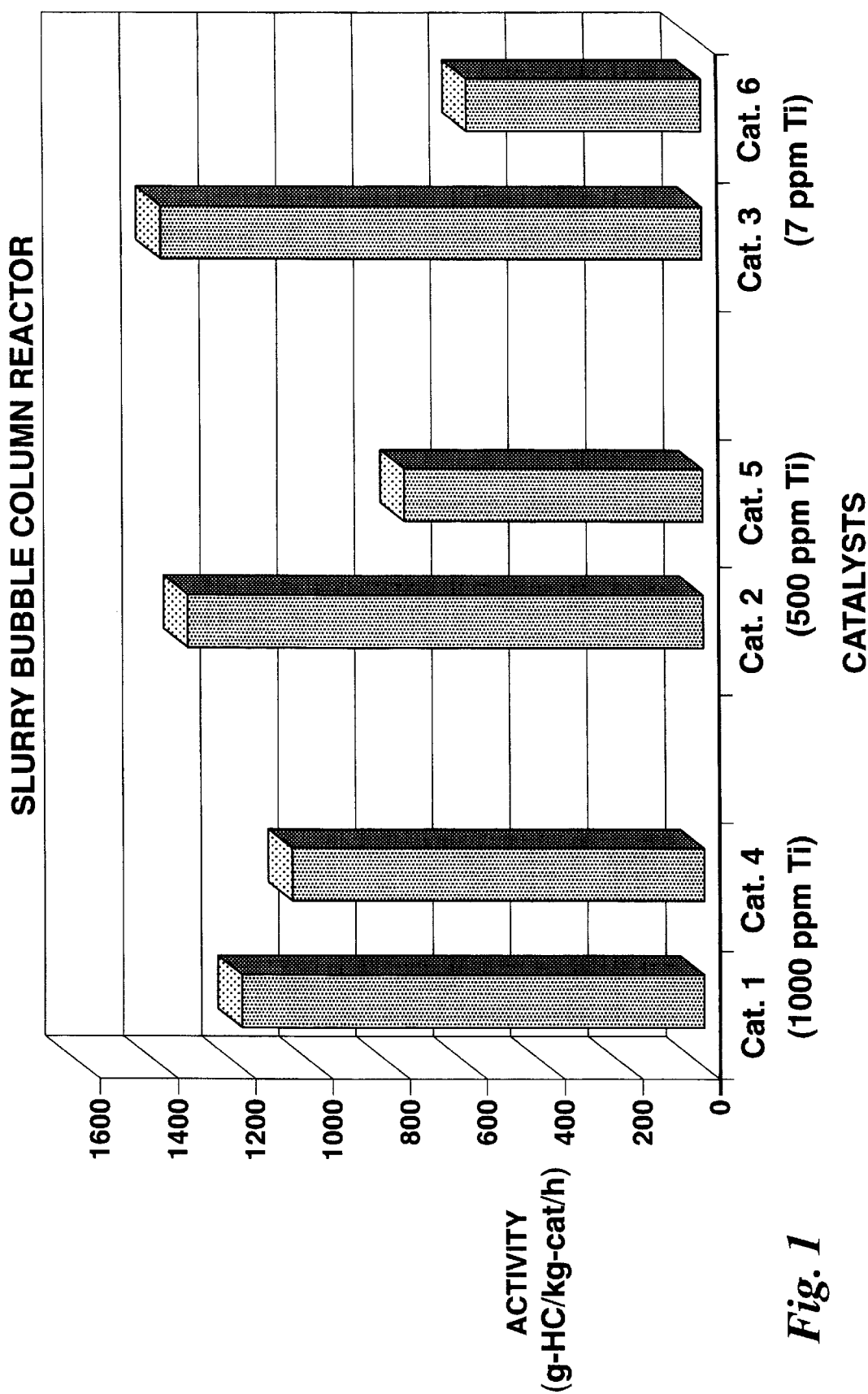
FIG. 1 provides a graph comparing the effect of titanium dopant concentrations on the activities of ruthenium-promoted catalysts and "nonpromoted" catalysts for Fischer-Tropsch synthesis processes conducted in an SBCR. Each test involved 15–25 grams of catalyst which was sieved to 400–150 mesh, calcined, and then reduced/activated outside of the SBCR system. Each Fischer-Tropsch reaction test was conducted at 450 psig and 230° C. using a synthesis gas flow rate of 15 liters per minute. The synthesis gas was diluted with 60% nitrogen and had a $H_2$:CO ratio of 2.

The present invention provides supported cobalt catalysts which are well suited for use in Fischer-Tropsch synthesis. These catalysts are particularly well suited for use in slurry bubble column reactor processes. Examples of preferred, general catalyst compositions provided by the present invention include, but are not limited to: (a) cobalt, without any noble metal or near noble metal promoter, preferably supported on a doped γ-alumina, and (b) cobalt promoted with one or more selectivity promoters (preferably an alkali promoter and/or a rare earth oxide such as lanthana), but without a noble metal or near noble metal promoter, and preferably supported on a doped γ-alumina.

Preferred catalyst compositions comprise (per 100 parts by weight of support): from about 10 to about 65 pbw cobalt; from about 0.1 to about 8 pbw potassium (when present); and from about 0.5 to about 8 pbw lanthana (when present). The catalysts will most preferably comprise (per 100 parts by weight of support): from about 17 to about 45 pbw (more preferably about 20 to about 40 pbw, and most preferably about 30 pbw) cobalt; from about 0.2 to about 1.0 pbw potassium (when present); and/or from about 0.9 to about 2.1 pbw lanthana (when present).

The Catalyst Support

The support employed in the inventive catalyst will preferably be γ-alumina. We have determined that, for cobalt catalysts used in both fixed bed and a slurry bubble column reactor systems, the particular support employed plays a major role in influencing overall hydrocarbon production rate (i.e., catalyst activity) with little or no effect on product selectivity. Catalyst activities generally rank in the following order: $Al_2O_3 > SiO_2 \gg TiO_2$. The source of the alumina and the pretreatment procedures used also play major roles in determining the performance of the resulting, cobalt-based, Fischer-Tropsch catalysts.

Titania-supported cobalt catalysts, with or without promoters, were found to have poor Fischer-Tropsch synthesis properties in both the fixed bed and SBCR systems. Compared to γ-alumina and silica, titania supports have much lower surface areas and pore volumes. Thus, they do not readily retain high cobalt loadings.

Although silica supports have relatively high surface areas, silica-supported cobalt catalysts also provided low Fischer-Tropsch synthesis performance. Silica-supported cobalt catalysts are unstable in reaction conditions, such as those usually encountered in Fischer-Tropsch reaction systems, where a significant amount of water is present. The formation of cobalt-silica compounds under these conditions is believed to cause this lower performance. To prevent or at least slow down silicate formation, the silica surface must typically be coated with oxide promoters, such as $ZrO_2$, prior to cobalt impregnation.

Characteristics and Preparation of Preferred Alumina Supports

The catalyst support employed in the present invention is preferably a γ-alumina support having: a low level of impurities, especially sulfur (preferably less than 100 ppm sulfur); a spheroidal shape; an average particle size in the range of from about 10 to about 150 μm (most preferably from about 20 to about 80 microns); a BET surface area, after calcination, in the range of from about 200 to about 260 $m^2/g$; and a porosity in the range of from about 0.4 to about 1.0 $cm^3/g$.

The alumina support is preferably produced from relatively high purity, synthetic boehmite. As discussed hereinbelow, the boehmite can be formed from aluminum alkoxide of the type obtained as a byproduct in the manufacture of synthetic fatty alcohols. Alternatively, suitable, high-purity boehmite materials can be formed from aluminum alkoxides produced by alcohol/aluminum metal reaction processes.

The aluminum alkoxide is preferably hydrolyzed to produce high purity, synthetic, monohydrate alumina. Next, this material is preferably spray-dried to yield highly porous, spherical boehmite particles of relatively high surface area. The particulate boehmite material is preferably then sieved to remove fines and large particles so that a desired particle size range is obtained (most preferably from about 20 to about 80 microns). The sieved material is calcined to convert the boehmite particles to a γ-alumina support material having the desired surface area and porosity. The boehmite material will preferably be calcined at a temperature of at least 350° C. (more preferably from about 400° C. to about 700° C. and most preferably about 500° C.) for a period of from about 3 to about 24 hours (more preferably from about 5 to about 16 hours and most preferably about 10 hours). The desired calcination temperature is preferably reached by slowly heating the system at a rate of about 0.5–2.0° C./minute.

Examples of commercially-supplied boehmite materials suitable for forming the preferred γ-alumina supports include, but are in no way limited to, the CATAPAL and PURAL aluminas supplied by Condea/Vista. As discussed below, commercial materials of this type are particularly effective when intentionally produced to have certain targeted titanium "impurity" levels. Product quality reports for the CATAPAL aluminas indicate that these products, as presently produced and sold, can have titania impurity levels varying all the way up to 3000 ppm of elemental titanium by weight. The PURAL products, on the other hand, typically have varying titanium impurity levels of up to about 600 ppm.

Doping of γ-Alumina Supports

As shown hereinbelow, we have discovered that the presence of a controlled amount of dopant (preferably a titanium dopant) in the γ-alumina support unexpectedly and surprisingly improves significantly the activities of "nonpromoted", cobalt-on-alumina Fischer-Tropsch catalysts. As used herein, the term "nonpromoted" means simply that the catalyst is not promoted with any noble or near noble metals. The term does not exclude other types of promoters (e.g., potassium and/or lanthana). The phrase "near noble metal," as used herein, encompasses rhenium and, although not practical for use as a promoter, also encompasses technetium.

The titanium dopant should be present in the γ-alumina support in an amount, expressed as elemental titanium, of at least 500 (preferably of at least 800) parts per million (ppm) by weight. The dopant will more preferably be present in the support in an amount, expressed as elemental titanium, in the range of from about 800 ppm to about 2000 ppm by weight and will most preferably be present in an amount in the range of from about 1000 to about 2000 ppm. The titanium dopant can be added at substantially any time but will most preferably be added prior to crystallization of the boehmite.

As is well known in the art, one method of producing synthetic boehmite materials utilizes aluminum alkoxides recovered as byproducts of certain processes (e.g., the Ziegler Process) employed for manufacturing synthetic fatty alcohols. The Ziegler Process typically comprises the steps of. (1) reacting high-purity alumina powder with ethylene and hydrogen to produce aluminum triethyl; (2) polymerizing ethylene by contacting it with the aluminum triethyl, thus forming aluminum alkyls; (3) oxidizing the aluminum alkyls with air to produce aluminum alkoxides; and (4) hydrolyzing the aluminum alkoxides to produce alcohols and an alumina byproduct. The oxidation step of the Ziegler process is typically catalyzed by an organic titanium compound which is itself converted to titanium alkoxide. The titanium alkoxide remains with, and is co-hydrolyzed with, the aluminum alkoxide, thus producing an alumina byproduct which is incidentally "doped" with a small amount of titania.

Another process for forming synthetic boehmite utilizes aluminum alkoxide produced by reacting an alcohol with a highly pure aluminum powder. The aluminum alkoxide is hydrolyzed to produce an alcohol, which is recycled for use in the alkoxide formation step, and alumina. Because this process does not involve an oxidation step, the alumina product typically does not contain titanium. However, for purposes of the present invention, any desired amount of titanium dopant can be included in the alumina product by, for example, adding a titanium alkoxide to, and co-hydrolyzing the titanium alkoxide with, the aluminum alkoxide. If desired, the same process can be used to add other dopants such as, for example, silica, lanthanum, barium, etc.

Heretofore, support manufacturers and catalyst users have simply considered titania, if present in the alumina support, to be a harmless impurity. Of the commercial synthetic boehmite products presently available in the market, some are produced by the Ziegler process, others are produced by the above-described aluminum alkoxide hydrolysis process, and still others are produced by a combination of these processes wherein the resulting products or product precursors are blended together. Such products are sold and used interchangeably, without regard to the amount, if any, of titania present.

Thus, the amount of titanium present in commercial γ-alumina supports can vary from 0 ppm to as high as 3000 ppm titanium by weight or more. Titanium concentrations can also vary significantly between different batches of the same commercial product.

As depicted in FIG. 1, titania has a significant detrimental effect on the activities of ruthenium-promoted, cobalt-on-alumina catalysts employed in slurry bubble column reactors. FIG. 1 shows the activities (g-HC/kg-cat/hr) of three ruthenium-promoted catalysts (catalysts 1, 2, and 3) which were produced and tested as described hereinbelow in Example 1. Catalysts 1, 2, and 3 were identical in all respects except that: catalyst 3 was formed on a γ-alumina support found to have a titania concentration, expressed as titanium, of about 7 ppm by weight; catalyst 2 was formed on a γ-alumina support found to have a titanium concentration of about 500 ppm; and catalyst 1 was formed on a γ-alumina support found to have a titanium concentration of about 1000 ppm. As the amount of titania in the support increased, the activities of the catalysts, which began at about 1400 for catalyst 3, declined to about 1322 for catalyst 2, and to about 1195 for catalyst 1. Thus, any preference in the art as to the presence of titanium would heretofore have been that no titanium be included in the γ-alumina support.

We have discovered, however, that, in contrast to the detrimental effect of titanium on the activities of "noble metal-promoted" catalysts employed in slurry bubble column reactors, the activities of "nonpromoted", cobalt-on-alumina catalysts, in all Fischer-Tropsch reaction systems, are unexpectedly and surprisingly improved when controlled amounts of dopant are present in the catalyst supports. The inventive, "non-promoted" catalysts have activities at least approaching those of catalysts promoted with noble metals. Moreover, because they need not be promoted with noble metals, the inventive catalysts cost much less to produce. Thus, our invention significantly reduces the cost of Fischer-Tropsch processes, particularly those processes conducted in slurry bubble column and other three-phase reaction systems wherein catalyst attrition losses are high.

Catalyst Preparation

Although other methods of preparation can be used, the catalytic components of the inventive catalysts are preferably added to the support by totally aqueous impregnation using appropriate aqueous solution compositions and volumes to achieve incipient wetness of the support material with the desired component loading(s). Promoted catalysts are most preferably prepared by totally aqueous co-impregnation. Examples of typical promoters include, but are not limited to: metal oxides, such as oxides of Zr, La, K, and other oxides of elements from Groups IA, IIA, IVA, VA, and VIA.

The totally aqueous impregnation of cobalt onto the support, with or without one or more desired promoters, is preferably accomplished by the steps of: (a) calcining the alumina support in the manner described above; (b) impregnating the support with an aqueous solution of cobalt nitrate, using a sufficient quantity of the solution to achieve incipient wetness with the desired loading of cobalt; (c) drying the resulting catalyst precursor for about 5–24 hours at approximately 80–130° C., with moderate mixing, to remove solvent water and obtain a dried catalyst; and (d) calcining the dried catalyst in air or nitrogen by slowly raising the temperature of the system at a rate of about 0.5–2.0° C. per minute to approximately 250–400° C. and then holding for at least 2 hours to obtain the oxide form of the catalyst. Multiple impregnation/coimpregnation steps (b) can be used when higher cobalt loadings are desired.

Alkali (e.g., potassium) and/or rare earth oxide (e.g., lanthana)-promoted catalysts can be prepared, for example, by dissolving potassium nitrate [$KNO_3$], lanthana nitrate [$La(NO_3)_3 \cdot 6H_2O$], and/or other precursors in the same solution which contains the cobalt precursor. Alkali promoters, particularly potassium, can significantly improve product selectivity and reduce methane production. Moreover, when employed in proper amounts, the alkali promoters do not substantially reduce catalyst activity. The addition of a lanthana ($La_2O_3$) promoter can enhance the attrition resistance of the catalyst. The improved attrition resistance provided by the addition of $La_2O_3$ is not detrimental to Fischer-Tropsch activity, or to Fischer-Tropsch selectivity. Preferred alkali and lanthana concentration ranges are provided hereinabove.

Catalyst Activation

To provide optimum performance, it is presently preferred that the catalyst be activated by reducing the catalyst in a hydrogen-containing gas by slowly increasing the temperature of the catalyst, preferably at a rate of about 0.5–2.0° C./minute, to approximately 250–400° C. (preferably about 350° C.) and holding at the desired temperature for at least 2 hours. After reduction, the catalyst is preferably cooled in flowing nitrogen.

The reducing gas preferably comprises from about 1% to 100% by volume of hydrogen, with the remainder (if any) being an inert gas, typically nitrogen. The reducing gas is preferably delivered at a rate of about 2–4 (preferably about 3) liters per hour per gram of catalyst. The reduction procedure is preferably conducted in a fluidized bed reactor vessel. The reduction procedure is most preferably conducted at conditions (i.e., temperature, flow rate, hydrogen concentration, etc.) effective to ensure that a very low water vapor partial pressure is maintained during the procedure.

As shown hereinbelow, this activation procedure unexpectedly enhances the activity of the inventive "non-promoted" cobalt catalysts.

The Fischer-Tropsch Reaction Process

The catalysts prepared and activated in accordance with the present invention can be employed in generally any Fischer-Tropsch synthesis process. Where applicable (e.g., for SBCR systems or continuous stirred tank reactor (CSTR) systems), the catalyst will preferably be slurried in a Fischer-Tropsch wax or in a synthetic fluid (e.g., a $C_{30}$ to $C_{50}$ range isoparaffin polyalphaolefin such as that available from Chevron under the name SYNFLUID) having properties similar to those of Fischer-Tropsch wax. The catalyst slurry will preferably have a catalyst concentration in the range of from about 5% to about 40% by weight based on the total weight of the slurry.

The synthesis gas feed used in the reaction process will preferably have a $CO:H_2$ volume ratio of from about 0.5 to about 3.0 and will preferably have an inert gas (i.e., nitrogen, argon, or other inert gas) concentration in the range of from 0 to about 60% by volume based on the total volume of the feed. The inert gas is preferably nitrogen.

Prior to initiating the reaction process, the activated catalyst will most preferably be maintained in an inert atmosphere. Before adding the catalyst thereto, the slurry fluid will preferably be purged with nitrogen or other inert gas to remove any dissolved oxygen. The slurry composition will also preferably be transferred to the reaction system under an inert atmosphere.

A particularly preferred SBCR reaction procedure comprises the steps of: (a) filling the SBCR, under an inert atmosphere, with the activated catalyst slurry; (b) heating and pressurizing the SBCR, under an inert atmosphere, to the desired pretreatment conditions (preferably a temperature in the range of from about 220° C. to about 250° C. and a pressure in the range of from about 50 to about 500 psig); (c) replacing the inert gas with hydrogen and holding the system at these conditions for from about 2 to about 20 hours; (d) purging the system with inert gas and lowering the reaction system temperature, if necessary, to a point at least about 10° C. below the desired reaction temperature; (e) carefully replacing the inert gas with the desired synthesis gas; and (f) heating and pressurizing the reaction system, as necessary, to a desired operating temperature, preferably in the range of from about 190° C. to about 300° C., and a desired operating pressure, preferably in the range of from about 50 to about 900 psig.

Cobalt Catalysts Without Noble Metal Promotion

It as long been believed that noble or near noble metal promotion is necessary to provide cobalt catalysts which are truly viable for commercial Fischer-Tropsch applications. Heretofore, the accepted view in the art has been that a nonpromoted $Co/Al_2O_3$ catalyst will only be from 50% to less than 25% as active as an otherwise identical catalyst promoted with one or more noble metals. U.S. Pat. No. 5,157,054 and other references discuss the necessity of using ruthenium or other promoters to obtain acceptable performance. However, the present invention unexpectedly and surprisingly provides "nonpromoted", cobalt-on-alumina catalysts having activities at least approaching these of cobalt catalysts promoted with noble metals. As will be apparent to those skilled in the art, eliminating the use of noble metal promoters without significantly decreasing catalyst performance greatly enhances the cost effectiveness of the Fischer-Tropsch process, particulary in reaction systems characterized by higher catalyst attrition losses.

Figure 2:
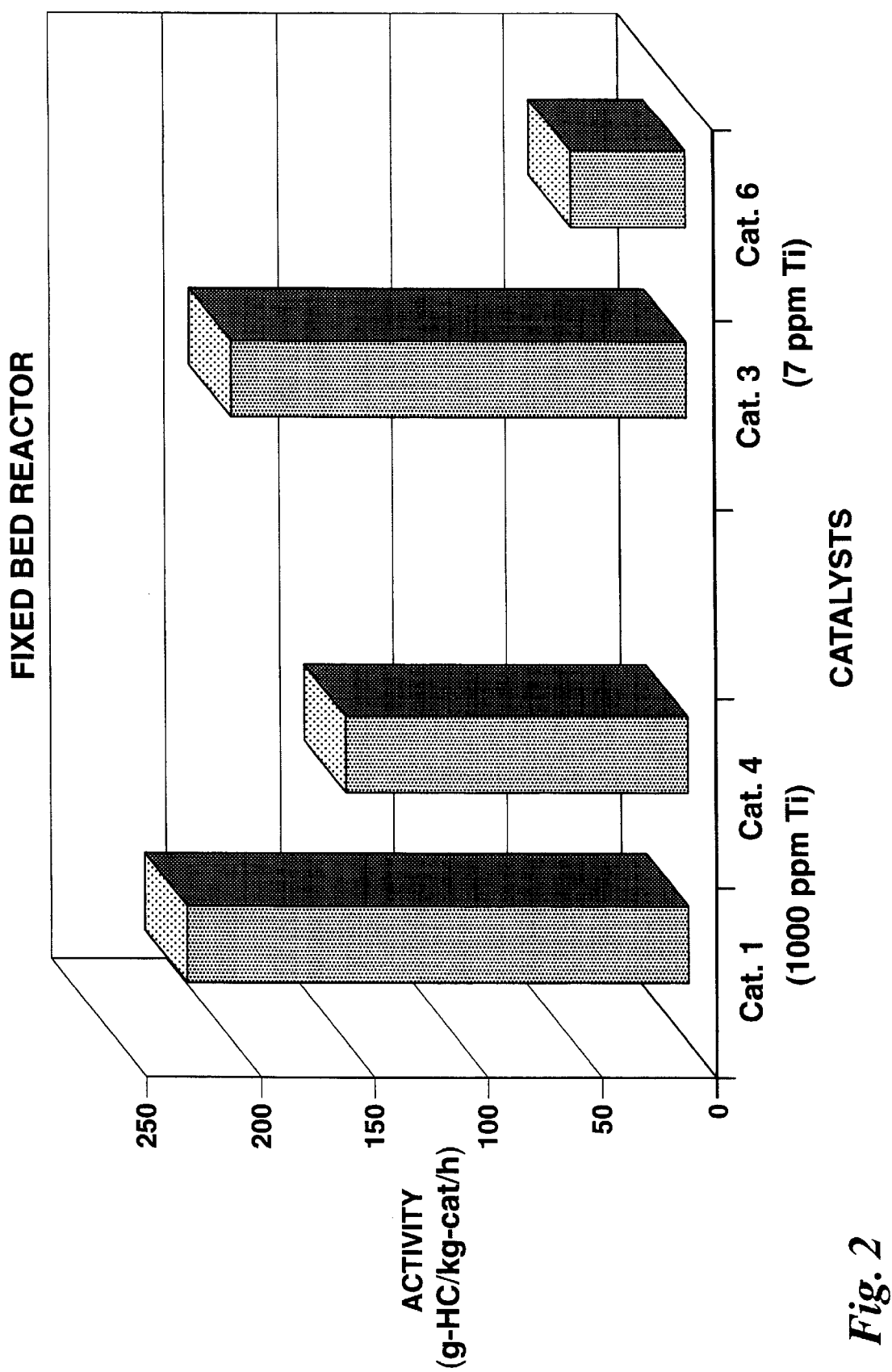
FIG. 2 provides a graph comparing the effects of titanium dopant concentrations on the activities of ruthenium-promoted catalysts and "nonpromoted" catalysts for Fischer-Tropsch synthesis conducted in a fixed bed reactor. In each case, the Fischer-Tropsch reaction was conducted at a pressure of 1 atmosphere, a temperature of 220° C., and a $H_2$/CO ratio of 2.

As depicted in FIGS. 1 and 2, the tests described hereinbelow amazingly show that the nonpromoted, cobalt-on-alumina catalysts produced and activated in accordance with the present invention perform at levels comparable to highly desirable, ruthenium-promoted catalysts. These results were unexpectedly obtained primarily through the use of doped γ-alumina supports. However, The catalyst activation procedure used, particularly the maintenance of a very low water vapor partial pressure during the reduction process, also surprisingly enhanced the activity of the nonpromoted, cobalt-on-alumina catalysts.

The amount of dopant employed will preferably be an amount effect to provide a catalyst activity which is at least 60% (preferably at least 70%, more preferably at least 80%, and most preferably at least 90%) of that of an otherwise identical catalyst promoted with ruthenium in a ruthenium to cobalt weight ratio of 1:40. The amount of dopant required to obtain a desired activity level for any given application can be readily determined.

As indicated above, the dopant is preferably employed in an amount of at least 500 ppm (more preferably from about 800 ppm to about 2000 ppm), based on the total weight of the γ-alumina support, and is most preferably added prior to the crystallization of the boehmite precursor.

Low Water Vapor Partial Pressure

As to the beneficial results obtained by maintaining a very low water vapor partial pressure during the reduction process, it is believed that the presence of water vapor in the activation system promotes the formation of certain cobalt-alumina compounds which are very difficult or impossible to reduce. Temperature programmed reduction studies conducted by Applicants indicate that, in contrast to nonpromoted catalysts, the presence of noble metal promoters such as ruthenium appear to enhance the reduction process in a manner which may counteract the deleterious effects of water vapor.

When activating a nonpromoted cobalt catalyst in accordance with the present invention, the partial pressure of water vapor in the activation system will preferably be maintained at or below a level effective for increasing the activity of the catalyst. The water vapor partial pressures effective for providing such results can readily be determined for any nonpromoted, cobalt-on-alumina catalyst. Although the values necessary to obtain the desired results may vary depending upon the specific catalyst selected, it is presently preferred that the partial pressure of water vapor in the activation system be maintained below 0.1 atmospheres.

EXAMPLES

In the following examples 1–4, certain cobalt-on-alumina catalysts were prepared and then tested in various Fischer-Tropsch reaction systems. Before testing, each catalyst was reduced in pure hydrogen by slowly increasing the temperature of the catalyst, at a rate of about 1.0° C. per minute, to about 350° C. and holding at this temperature for 10 hours. The hydrogen was delivered at a rate of about 3 liters per hour per grain of catalyst. After reduction, the catalyst was cooled in flowing nitrogen.

For slurry bubble column reactor (SBCR) tests conducted in examples 1–4, the reduction procedure was conducted in a fluidized bed reactor. After cooling to ambient temperature, the catalyst was weighed, slurried in SYNFLUID, and then transferred to the SBCR under an inert atmosphere. The SBCR tests were then conducted at 230° C. and 450 psig using 900 sl/hr of syngas and from 15 to 25 grams of reduced catalyst. The syngas contained 60% nitrogen and had a $H_2/CO$ ratio of 2. In each case, the SBCR results cited are those obtained after 24 hours on-stream.

For fixed bed micro-reactor (FBR) tests, the catalyst was reduced in-situ using the same procedure just described. Prior to the introduction of syngas, the reduced catalyst was cooled to about 10–15° C. below the reaction temperature. The FBR tests were then conducted under differential conditions (i.e. low conversion) at atmospheric pressure and 220° C. using from 0.5 to 1.0 grams of catalyst and a $H_2/CO$ ratio of 2. In each case, the FBR results cited are those obtained after 24 hours on-stream.

EXAMPLE 1

Effect of Titania Impurities on the Activities of Ru-Promoted Catalysts in a Slurry Bubble Column Reactor (SBCR)

The following ruthenium-promoted, cobalt-on-alumina catalysts were identically prepared and had identical loadings of cobalt and ruthenium. The catalysts differed only with respect to the amounts of titanium "impurity" contained in the γ-alumina supports. The aluminas were all manufactured by Condea/Vista.

CATALYST 1: (Ru-promoted cobalt catalyst on CATAPAL B alumina with 20 wt % cobalt and 0.5 wt % ruthenium)

Preparation Procedure:

CATAPAL B alumina, supplied by Condea/Vista in the boehmite form, was calcined at 500° C. for 10 hrs to convert it to γ-alumina. It was then preserved to 400–170 mesh (i.e., a particle size range of from more than 38 microns to less than 88 microns) and impregnated using an amount of an aqueous solution of cobalt nitrate [$Co(NO_3)_2 6H_2O$] and ruthenium (III) nitrosylnitrate [$Ru(NO)NO_3)_3 \cdot xH_2O$] appropriate to achieve incipient wetness (ca. 1.2 ml/g) with the desired loadings of Co. and Ru. The catalyst precursor was then dried in air at 115° C. for 5 hours and calcined in air at 300° C. for 2 hours (with a heating rate of ca. 1° C./min to 300° C.).

Reduction Procedure before Reaction:

The catalyst was reduced in 3000 cc/g/hr of pure hydrogen by heating at 1° C./min to 350° C. and holding for 10 hrs.

Each of the following catalysts 2 and 3 were prepared and reduced in the same manner as catalyst 1. The specific supports employed in catalysts 2 and 3 were as follows:

CATALYST 2: PURAL SB support supplied by Condea/Vista.

CATALYST 3: PURAL SB1 support supplied by Condea/Vista.

The particular CATAPAL B support material employed in catalyst 1 was determined to contain an amount of titania "impurity" of about 1000 ppm by weight (expressed as ppm by weight of titanium) which was incidentally added as part of the Ziegler Process prior to the crystallization of the boehmite. In contrast, the particular PURAL SB support material employed in catalyst 2 had been formed by a blending process and was found to contain about 500 ppm of titanium. The PURAL SB1 support employed in catalyst 3 was identical to the PURAL SB support except that efforts were made to prevent the addition of titanium. An elemental analysis showed that the PURAL SB1 support contained only 7 ppm of titanium. The crystallite characteristics of the CATAPAL B, PURAL SB and PURAL SB1 supports were substantially identical.

FIG. 1 shows the activities (expressed in g-HC/kg-cat/hr) exhibited by catalysts 1–3 in an SBCR at the end of 24 hours on-stream. A comparison of catalysts 1–3 illustrates the detrimental effect of titania on the activities of ruthenium-promoted, cobalt-on-alumina catalysts. As the amount of titania in the support increased, activity declined significantly. Catalyst 3 provided an activity of about 1400 and had selectivities (%C) of 80.5 for $C_5^+$ and 8.4 for $CH_4$. Catalyst 2 provided an activity of about 1322 and had selectivities for $C_5^+$ and $CH_4$ of 81.9 and 8.5, respectively. Catalyst 1 provided an activity of about 1195 and had selectivities of 82.2 ($C_5^+$) and 8.2 ($CH_4$).

EXAMPLE 2

Effect of Titania Doping on the Activities of Non-Promoted Catalysts in a Slurry Bubble Column Reactor The following catalysts 4–6 were respectively identical to catalysts 1–3, except that catalysts 4–6 did not include any promoters.

CATALYST 4 (Non-promoted, alumina supported catalyst with 20 wt % Cobalt)

Preparation Procedure:

CATAPAL B alumina, supplied by Condea/Vista in the boehmite form, was calcined at 500° C. for 10 hrs to convert it to γ-alumina. It was then presieved to 400–170 mesh (i.e, a particle size range of from more than 38 microns to less than 88 microns) and impregnated using an amount of an aqueous solution of Co nitrate [$Co(NO_3)_2 \cdot 6HO$] appropriate to achieve incipient wetness (ca. 1.2 ml/g) with the desired loading of Co. The catalyst precursor was then dried in air at 115° C. and calcined in air at 300° C. for 2 hours (heating rate of ca. 1° C./min to 300° C.).

Reduction Procedure before Reaction:

The catalyst was reduce in a pure hydrogen flow of 3000 cc/g/hr by heating at 1° C./min to 350° C. and holding for 10 hours.

Each of the following catalysts 5 and 6 were prepared and reduced in the same manner as catalyst 4. The specific supports employed in catalysts 5 and 6 were as follows:

CATALYST 5: PURAL SB as described above.

CATALYST 6: PURAL SB1 as described above.

Catalysts 4–6 were tested in a slurry bubble column reactor. Their activities (expressed in g-HC/kg-cat/hr) after 24 hours-on-stream are also shown in FIG. 1. In stark contrast to the results obtain with ruthenium-promoted catalysts 1–3, the presence of titania in the γ-alumina support unexpected and surprisingly improved significantly the activities of the non-promoted catalysts. Catalyst 6 (7 ppm Ti) provided an activity of about 606 and had selectivities (%C) of 85.6 ($C_5^+$) and 5.2 ($CH_4$). Catalyst 5 (500 ppm Ti) provided an activity of about 775 and had selectivities of 84.0 ($C_5^+$) and 6.2 ($CH_4$). Catalyst 4 (1000 ppm Ti) provided an activity of about 1032 and had selectivities of 86.5 ($C_5^+$) and 6.0 ($CH_4$). Thus, in this SBCR test, the activity of non-promoted catalyst 4 was 86% of that provided ruthenium-promoted catalyst 1. Further, the selectivities provided by catalyst 4 were significantly superior to those of the ruthenium-promoted catalysts.

EXAMPLE 3

Effect of Titania Doping on the Activities of Non-Promoted Catalysts in a Fixed Bed Reactor Ruthenium-promoted catalysts 1 and 3 and non-promoted catalysts 4 and 6 were also tested in a fixed bed microreactor (FBR) under the conditions described above, (atmospheric pressure and a temperature of 220° C.). FIG. 2 illustrates again the significant, unexpected, and surprising effect of titania doping on the activities of the non-promoted cobalt catalysts. While the activities exhibited by the two ruthenium-promoted catalysts remained relatively constant (220 and 200 g-HC/kg-cat/h for Catalysts 1 and 3, respectively) the activity of the titanium-doped (1000 ppm), non-promoted catalyst 4 was three times higher than that of non-doped (7 ppm), non-promoted catalyst 6. Moreover, whereas the activity of non-promoted catalyst 6 (7 ppm Ti) was only about 25% of that of promoted catalyst 3, non-promoted catalyst 4 (1000 ppm Ti) amazingly provided an activity level which was about 75% of that of catalyst 3.

EXAMPLE 4

Effect of Titania Doping on the Performances of Ru-Promoted and Non-Promoted Catalysts in a Continuously Stirred Tank Reactor (CSTR)

In order to ascertain whether the SBCR results shown in FIG. 1 represented the intrinsic activities of the non-promoted, cobalt-on-alumina catalysts, ruthenium-promoted Catalyst 1 and non-promoted Catalyst 4 were tested in a continuously stirred tank reactor (CSTR). As discussed above, both catalysts were supported on CATAPAL B alumina containing about 1000 ppm by weight of titanium. In a CSTR, mass transfer limitations are substantially negligible such that true intrinsic kinetics can be measured. The performance of the two cobalt catalysts in the CSTR was evaluated under reaction conditions substantially similar to those employed in the SBCR. Amazingly, in accordance with the unexpected and surprising results obtained in the SBCR and FBR tests, the activities exhibited by promoted catalyst 1 and nonpromoted catalyst 4 in the CSTR were, within experimental error, substantially the same. At 240° C. and 450 psig, ruthenium-promoted Catalyst 1 and non-promoted Catalyst 4 exhibited activities of 1390 and 1330 (g-HC/g-cat/h), respectively.

EXAMPLE 5

Temperature Programmed Reduction Studies of the Effects of Titania Doping

It is well known that noble metal promoters enhance the reducibility of cobalt. The effects of titania on the reducibilities of non-promoted catalysts 4 and 6 were determined using temperature programmed reduction (TPR). The results were compared to TPR results obtained for ruthenium-promoted catalysts 1 and 3.

In each case, the calcined catalyst was initially dried, under an argon flow, at 120° C. for 30 minutes to remove water. In the TPR tests, a 5% $H_2$/Ar gas mixture was used as the reducing gas. The reducing gas flow rate was 30 $cm^3$/min. During the reduction test, the catalyst was heated to 900° C. at a rate of 5° C./min. The effluent gas was delivered through a cooling trap (less than 50° C.) to condense and collect water generated by the reduction process. The amount of $H_2$ consumed by the catalyst was monitored, using a thermal conductivity detector (TCD), and recorded as a function of temperature. From this data (and assuming the oxide to be in the form of $Co_3O_4$), the total reducibility of each catalyst, up to a temperature of 900° C., was determined and expressed as the percent of cobalt completely reduced. The percent reducibilities of catalysts 1, 3, 4, and 6 at 900° C. are shown in Table 1. Table 1 also provides the low and high reduction temperature peaks exhibited by each catalyst.

TABLE 1

Temperature Programmed Reduction Results

| Catalyst | Low Temperature Peak (° C.) | High Temperature Peak (° C.) | Reducibility (%) |
| --- | --- | --- | --- |
| Catalyst 1 | 253 | 483 | 98 |
| Catalyst 3 | 241 | 471 | 99 |
| Catalyst 4 | 238/322 | 587 | 99 |
| Catalyst 6 | 328 | 584 | 90 |

As expected, both of the ruthenium-promoted catalysts were almost totally reduced (98+%) under the conditions used in the TPR experiments. In addition, they reduced at lower temperatures than their non-promoted analogs. However, a comparison of the results obtained for the non-promoted catalysts shows, again, that titania doping provided a significant, beneficial effect. Like the ruthenium-promoted catalysts, the non-promoted catalyst having a doped support was completely (99%) reduced. However, the non-promoted catalyst having a no dopant was only 90% reduced.

It is believed that certain, hard-to-reduce, cobalt-alumina compounds can form during reduction, especially when, as is typically the case, the reduction system has a relatively high water vapor partial pressure. Noble metal promoters, which allow cobalt reduction at lower temperature, either help to prevent the formation of these compounds and/or enhance their reducibility. Our findings suggest that, for a non-promoted cobalt-on-alumina catalyst, the presence in the support of a controlled amount of dopant helps prevent the formation of cobalt-alumina compounds, thus improving the overall reducibility of the catalyst. This would explain the significant improvement in Fischer-Tropsch activity observed for nonpromoted, cobalt-on alumina catalysts having doped supports.

EXAMPLE 6

To test the effects of water vapor partial pressure during the reduction process, two different batches of the same nonpromoted, 20 wt % cobalt-on-alumina catalysts (i.e., a 50 g (lab size) batch and a 220 g batch) were reduced as set forth below and then tested in an SBCR.

Test 1: The 50 g (lab size) batch was reduced at 350° C. for 18 hours with 100% $H_2$ at a flow rate above 3 l/hr per gram of catalyst. The SBCR test was started with a charge of 15 g of the reduced catalyst. The reaction conditions were as follows: a temperature of 220° C., a pressure of 450 psig, a total gas flow rate of 900 sl/hr with 60% $N_2$, and a $H_2$/CO ratio of 2. The CO conversion was 13.6%, the hydrocarbon productivity (activity) was 0.66 g HC/g cat./hr, and the $CH_4$ selectivity was 3.2%.

Test 2: The 220 g batch of the same catalyst was reduced at the same conditions except that a hydrogen flow rate of 1.8 l/hr per gram of catalyst was used. The SBCR test was started with a 15 g charge of catalyst and was run under the same reaction conditions as in Test 1. The CO conversion was only 3.4%, with a hydrocarbon productivity (activity) of just 0.17 g HC/g cat./hr.

A re-reduction of the catalyst employed in Test 2, using a smaller batch, did not produce better results. The catalyst was irreversibly damaged during the first reduction. Additional large batch reductions (ca. 0.6–1 kg) produced similarly inactive or very low activity catalysts.

These results suggest that a higher water vapor partial pressure present during the reduction of the larger batches had a negative effect on the reducibility of the catalyst.

EXAMPLE 7

Following the unsuccessful, attempted reduction of large batches of the non-promoted Co/$Al_2O_3$ catalyst, and in view of the belief that the presence of a relatively high water vapor partial pressure during the initial stages of the reduction process was responsible for their low reducibility, it was suggested that higher reduction temperatures might provide improved reducibility. Hence, two new lab size batches (ca. 50 g) of the same unpromoted Co/$Al_2O_3$ catalyst tested in Example 6 were reduced at 410° C. and 380° C., respectively. In order to test the effect of high water vapor partial pressure, the hydrogen stream used for each reduction was saturated with water vapor by passing it through a saturator, at room temperature, before use in the reduction system.

The SBCR tests were again carried out at the same reaction conditions as described in Example 6. In spite of the different reduction temperatures used, each batch had a CO conversion activity of below 1%. The results showed that the high concentration of water in the hydrogen stream had a drastic effect on catalyst reducibility and that, under such conditions, the use of an increased reduction temperature did not improve the reducibility of the catalyst. The high water vapor partial pressure is believed to have caused the formation of cobalt-alumina compounds which were very difficult or impossible to reduce. The use of a higher reduction temperature seemed to actually promote the production of such compounds rather than enhance the reduction process.

Thus, the present invention is well adapted to carry out the objects and attain the ends and advantages mentioned above, as well as those inherent therein. While the invention has been described with a certain degree of particularity, it is manifest that many changes may be made without departing from the spirit and scope of this disclosure. It is understood that the invention is not limited to the embodiments set forth herein for purposes of exemplification.

What is claimed is:

1. A process for Fischer Tropsch hydrocarbon synthesis comprising the step of reacting a synthesis gas in the presence of a cobalt catalyst wherein:

said cobalt catalyst comprises cobalt supported on a γ-alumina support;

said cobalt catalyst is not promoted with any noble metals deposited on said γ-alumina support, is not promoted with rhenium or technetium deposited on said γ-alumina support, and is not promoted with titanium deposited on said γ-alumina support;

said γ-alumina support has an internal structure comprising γ-alumina and a controlled amount of a titanium dopant; and said controlled amount of said titanium dopant in said γ-alumina support is an amount effective for increasing the activity of said cobalt catalyst for said Fischer-Tropsch hydrocarbon synthesis.

2. The process of claim 1 wherein said controlled amount of said titanium dopant is an amount effective to render said cobalt catalyst at least 60% as active, for said Fischer-Tropsch hydrocarbon synthesis, as a promoted catalyst which is identical to said cobalt catalyst except that said promoted catalyst is promoted with ruthenium in a ruthenium to cobalt weight ratio of 1:40.

3. The process of claim 2 wherein said controlled amount of said titanium dopant is an amount effective to render said cobalt catalyst at least 70% as active as said promoted catalyst.

4. The process of claim 2 wherein said controlled amount of said titanium dopant is an amount effective to render said cobalt catalyst at least 80% as active as said promoted catalyst.

5. The process of claim 1 wherein said controlled amount of said titanium dopant, expressed as elemental titanium, is at least 500 ppm by weight of the total weight of said γ-alumina support.

6. The process of claim 1 wherein said controlled amount of said titanium dopant, expressed as elemental titanium, is in the range of from about 800 to about 2000 ppm by weight of the total weight of said γ-alumina support.

7. The process of claim 1 wherein said controlled amount of said titanium dopant, expressed as elemental titanium, is about 1000 ppm by weight of the total weight of said γ-alumina support.

8. The process of claim 1 further comprising the step, prior to said step of reacting, of activating said cobalt catalyst by reducing said cobalt catalyst in the presence of hydrogen and at a water vapor partial pressure effective to increase said activity of said cobalt catalyst.

9. The process of claim 8 wherein said water vapor partial pressure is in the range of from 0 to about 0.1 atmospheres.

10. The process of claim 1 wherein said step of reacting is conducted in a slurry bubble column reactor.

11. The process of claim 1 wherein:

said γ-alumina support is produced from synthetic boehmite; and said titanium dopant is added to said γ-alumina support prior to the crystallization of said boehmite.

12. The process of claim 1 wherein:

said γ-alumina support is formed from aluminum alkoxide which is hydrolyzed to produce an alumina product and said titanium dopant is added to said γ-alumina support by cohydrolyzing titanium alkoxide with said aluminum alkoxide in an amount effective to yield said controlled amount of said titanium dopant in said γ-alumina support.

13. The process of claim 1 wherein said cobalt is deposited on said γ-alumina support by totally aqueous impregnation using cobalt nitrate.

* * * * *